United States Patent [19]

Stevens

[11] 4,288,426

[45] Sep. 8, 1981

[54] SEROLOGICAL TEST FOR SYPHILIS

[75] Inventor: Roy W. Stevens, Schenectedy, N.Y.

[73] Assignee: Research Corporation, New York, N.Y.

[21] Appl. No.: 132,180

[22] Filed: Mar. 20, 1980

[51] Int. Cl.$^3$ .................. G01N 33/54; G01N 33/56
[52] U.S. Cl. ................... 424/1; 23/230 B; 424/8; 435/7
[58] Field of Search ............ 23/230 B, 915, 920; 424/1, 8, 12, 13; 435/7

[56] References Cited

U.S. PATENT DOCUMENTS

| | | | |
|---|---|---|---|
| 2,709,670 | 5/1955 | Ichelson | 424/13 X |
| 3,502,546 | 3/1970 | Thompson | 424/13 X |
| 3,600,494 | 8/1971 | Tomizawa | 424/13 |
| 3,882,224 | 5/1975 | Forgione | 424/8 |
| 3,949,065 | 4/1976 | Forgione | 424/13 X |
| 4,076,797 | 2/1978 | Davis | 424/13 X |
| 4,178,359 | 12/1979 | Mondabaugh | 424/1 |
| 4,201,763 | 5/1980 | Monthony | 23/230 B X |

OTHER PUBLICATIONS

Chemical Abstracts, 77:46489j (1972).

*Primary Examiner*—Sidney Marantz
*Attorney, Agent, or Firm*—Wyatt, Gerber, Shoup, Scobey & Badie

[57] ABSTRACT

Serological method of testing for *Treponema pallidum* antibodies in human serum which is diluted with physiological saline to a dilution of from 1:20 to 1:100 by incubating the diluted serum with a lysate of *T. pallidum* adsorbed on an inert adsorbent and detecting an antigen-antibody conjugate when antibodies are present.

8 Claims, 1 Drawing Figure

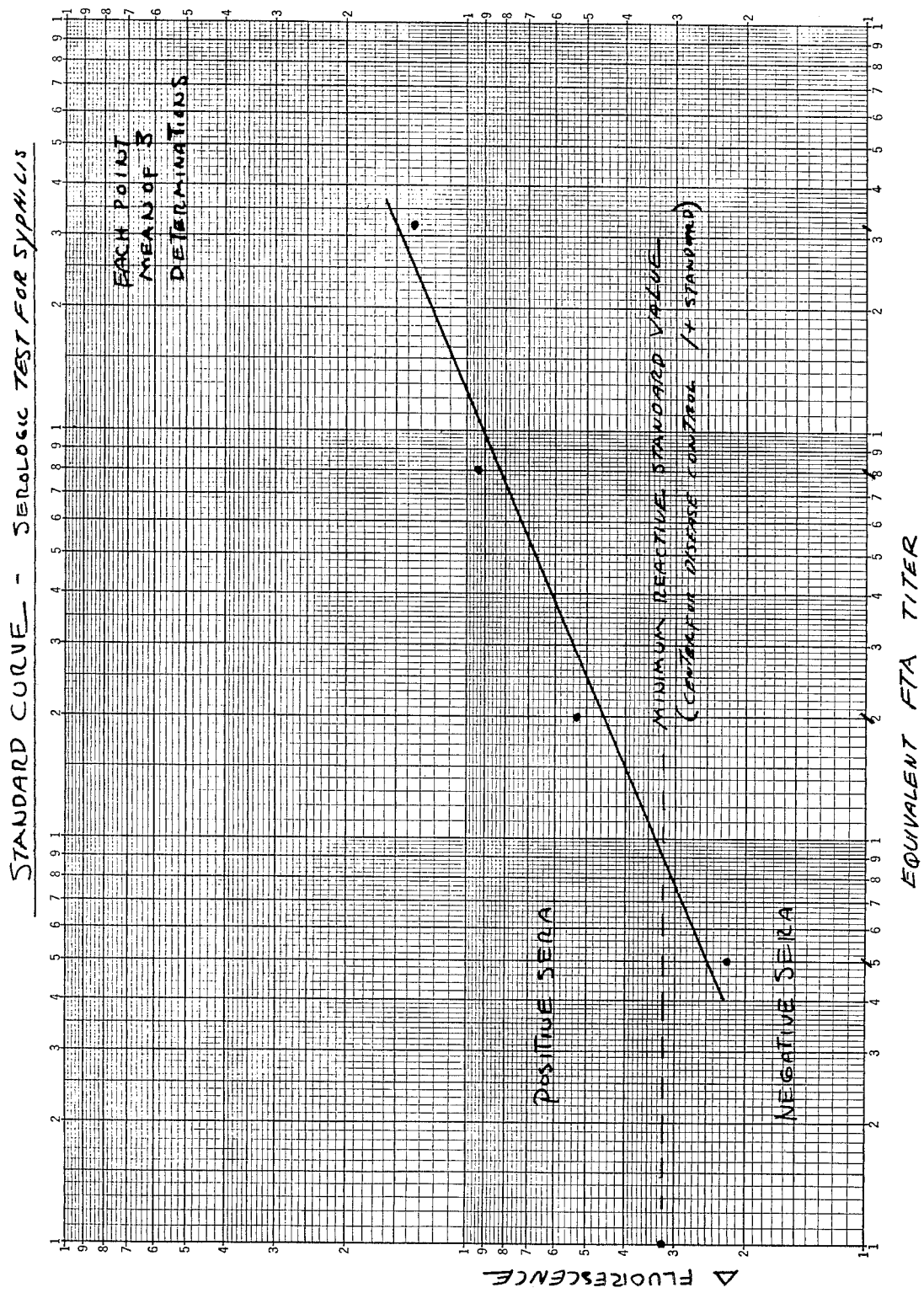

SEROLOGICAL TEST FOR SYPHILIS

FIELD OF THE INVENTION

This invention relates to serologic methods for determining the presence of antibody to *Treponema pallidum* (Tp) in human sera.

BACKGROUND OF THE INVENTION

The standard treponemal tests for syphilis in humans presently accepted by the United States Public Health Service are the fluorescent treponemal antibody-absorption (FTA-ABS) test and the microhemagglutination *Treponema pallidum* (MHA-Tp) test.

The FTA-ABS is a manual, indirect FA microscope technique utilizing whole Tp microorganisms which are air dried and acetone fixed on glass slides. A determination of a positive or negative result is made on the basis of the fluorescence observed by the technician. The test is routinely performed in large volume testing laboratories. However, it is avoided in smaller laboratories because in low volume it is not cost effective, and the technicians do not have the experience to make the subjective decisions between positive and negative results accurately. It is, however, the presently acknowledged standard.

The MHA-Tp test is an indirect hemagglutination test employing an ultrasonic lysate of Tp adsorbed on tannic acid treated red cells. The test is less sensitive than the FTA-ABS test, especially in early disease, and the working test reagent (Tp-red blood cells) is stable for only five days. Further, although it is easy to perform, it is difficult to read.

A test has now been developed which substantially alleviates the difficulties of the foregoing techniques. It is specific, sensitive, easy to perform, objective and quantitative.

THE INVENTION

A novel method has now been developed in which a Tp lysate is adsorbed on an inert adsorbent and incubated with the serum under test to form a detectable antigen-antibody conjugate when the test is positive.

For the preparation of the lysate, Tp may be eluted from rabbit tissue and isolated by standard procedures. If desired, it may be stored at about $-70°$ C. The Tp suspension is thawed and centrifuged at 1,000 xG for 5 minutes to sediment non-specific aggregates. The supernate is centrifuged at 12,500 xG for 90 minutes. The sedimented Tp are resuspended to a concentration of $5 \times 10^9$ organisms/ml in 0.05 M sodium carbonate buffer, pH 9.4, and solubilized by shell freezing in a dry ice-ethanol slush. The product is thawed quickly with gentle agitation in a 37° C. water bath. The freeze thaw cycle is repeated nine times. The cryolysate is extruded without foaming through a 23 gauge needle ten times with a glass syringe. The product is then adsorbed on an inert adsorbent, e.g. polystyrene latex, bentonite, cellulose acetate discs, or charcoal.

In the presently preferred procedure, the presence of the antigen-antibody conjugate is determined fluorometrically using an animal antibody to human immunoglobulins labeled with a fluorescent label. In accordance with the procedure, the serum may be absorbed with any one of the commercially available sorbents, e.g. 1:5 in FTA-ABS sorbent and then further diluted to 1:8 in a suitable buffer, e.g. tris(hydroxymethyl) aminomethane (Tris-HCl) at pH 8.2. The final dilution is then 1:40. In practice it may be from 1:20 to 1:100. The adsorbed Tp is placed in the dilution tube and the mixture shaken at ambient temperature for from 25 to 40 minutes. The Tp on the adsorbent is washed with a suitable buffer such as Tris-HCl and shaken for another 5 to 10 minutes. The mix is then shaken at ambient temperature for from 25 to 40 minutes with a fluorescein isothiocyanate labeled goat antibody to human immunoglobulins. It is washed with Tris-HCl buffer and the fluorescence determined. For optimum accuracy, it is preferred to measure the difference between the fluorescence of free adsorbent and adsorbent with adsorbed lysate, and to compare this difference with a standard curve of known positive titers. A region on the standard curve is known to represent positive and negative titers.

The FTA-ABS sorbent is an autoclaved 8 day culture of Reiter treponemes in NIH thioglycolate broth containing heated (56° C.-30 min) rabbit serum. The exact composition is described in Health Laboratory Science 4 5–8 (1967) and may be purchased from Difco Laboratories, Detroit, Michigan or Clinical Sciences, Inc. Whippany, New Jersey. The FTA-ABS sorbent reportedly removes nonspecific "group" treponemal antibody. If sorbent is used, the initial serum dilution should be 1 to 5 in FTA-ABS sorbent (0.02 ml serum plus 0.08 ml sorbent). To negate participation of human serum complex with rabbit tissue substances possibly remaining in the Tp lysate, another sorbing substance may be added by homogenizing normal rabbit testicular tissue in FTA-ABS sorbent in a final concentration of 1 mg tissue/ml sorbent (0.1% w/w), The MHA-Tp sorbent contains 0.1% rabbit tissue.

It is a special and unexpected advantage of this embodiment of the invention that the use of sorbents to remove extraneous factors from the serum under test may be omitted with no loss in accuracy.

While the foregoing procedure is presently preferred, the presence of the conjugate can be detected by any of the presently available methods. Generally, the procedure is to incubate the reaction product with a labeled antibody to human immunoglobulins. An anti-immunoglobulin G (heavy chain) is preferred although anti-whole globulin and anti IgM may also be employed. The selected antibody to human globulins can be labeled with a detectable radioactive element, an enzyme or a chemical which fluoresces when exposed to ultraviolet light. Typically, the animal antibody to human immunoglobulins will be obtained from goats, but other animal sources such as rabbit, guinea pig or mule may be used.

As illustrated above, the presently preferred label is fluorescein which is combined to the animal antibody to human immunoglobulins through an isothiocyanate link. Other fluorescent labels can also be employed. These include, for example, rhodamine and auramine.

The antibody to human IgG can also be labeled with a radioactive element or with an enzyme. The radioactive label can be detected by any of the currently available counting procedures. The preferred isotope labels are $^{14}C$, $^{131}I$, $^{125}I$ and $^{35}S$. The enzyme label can be detected by any of the presently utilized colorimetric, spectrophotometric or fluorospectrophotometric techniques. The enzyme is conjugated to the antibody to human immunoglobulins by reaction with bridging molecules, such as carbodiimides, diisocyanates, glutaraldehyde and the like. Many enzymes which can be used in these procedures are known and can be utilized. The preferred are peroxidase, B-glucuronidase, B-D-glucosidase, B-D-galactosidase, urease, glucose oxidase plus peroxidase, galactose oxidase plus peroxidase, alkaline phosphatase and acid phosphatase.

A number of enzyme labeled antibodies and substrate combinations are available for use. The exact reagent concentrations and volumes, reaction tissues, and spectrophotometer wavelengths selected will be determined using well established (published) guidelines. Enzyme labeled antibody and substrate combinations in use and commercially available include: peroxidase-4-aminoantipyrine; peroxidase-o-dianisidine; alkaline phosphatase-p-nitrophenyl phosphate; glucose-o-dianisidine. These reagents are available from Miles Laboratory, Elkhart, Indiana, and Sigma Chemical Co., St. Louis, Missouri.

A number of commercially available spectrophotometers and cuvette combinations are suitable for use in the practice of this invention.

The process of this invention, especially the preferred embodiments thereof, has a number of advantages compared to the standard methods.

The test is objective and does not require subjective interpretation of immunofluorescence intensities. Thus it eliminates the region about the 1+ results where FTA-ABS reproducibility is most difficult to obtain, even for experienced observers as observed by Kraus et al, J. Immunol. 106 1665 (1971).

The number of tests which can be performed by a single operator is two to four times higher than is possible with the FTA-ABS procedure. Moreover, since the interpretation is objective, and can be automated, inexperienced technicians can perform the test. It is, therefore, applicable to small clinical laboratories as well as large ones. The FTA-ABS test is not readily adaptable to automation since nonspecific background fluorescence or noise is difficult to eliminate.

There is no danger of runover which in the FTA-ABS test has the potential for changing a nonreactive smear to a reactive smear in seconds; Hunter et al, J. Clin. Microbiol. 9 163–166 (1979).

The manipulations of the test are generally safer. The FTA-ABS test as is known has a number of potentially dangerous manipulations.

Test dilutions as high as 1:100 can be employed in contrast to the usual dilution for the FTA-ABS procedure, thus avoiding the adverse influences of high concentrations of interfering serum constituents. Typically, the test dilutions are from 1:20 to 1:100. The preferred dilutions are 1:30 to 1:50 since these combine good sensitivity with economical operation.

The process of this invention permits marked improvement in accuracy compared with previous standards. The number of false positives is reduced without concomitant increases in false negatives. The often extreme social, personal and medical consequences of diagnoses for syphilis require the highest accuracy in differentiating infected from noninfected invividuals. This advance in technology substantially alleviates errors and questionable, equivocal or borderline findings, and is of major importance to the laboratorian, clinician and the patient.

The following nonlimiting examples are given by way of illustration only.

EXAMPLE 1

For the preparation of the T. pallidum antigen, Tp are eluted from infected rabbit testicular tissue according to standard procedures. The suspension is adjusted by darkfield microscope count to approximately $1 \times 10^9$ organisms/ml. If desired, the Tp suspension may be stored at $-70°$ C. For preparation of lysate, the suspension is thawed (if necessary) at room temperature and transferred to a $15 \times 100$ mm glass tube. The storage container is rinsed with NACL solution. The suspension is centrifuged at $1000 \times G$ for 5 minutes at room temperature to sediment nonspecific aggregates. The supernate is transferred to $10 \times 75$ mm hard glass centrifuge tubes and centrifuged at $12,500 \times G$ for 90 minutes at $5°$ C. The sedimented Tp are resuspended by pipette in one-half the original volume with 0.05 M carbonate-bicarbonate buffer pH 9.6 and solubilized by shell freezing in a dry ice—ethanol slush. The product is thawed quickly with gentle agitation in a $37°$ C. water bath. The freeze-thaw cycle is repeated nine times. The cryolysate is extruded without foaming through a 23 gauge needle attached to a 0.5 ml syringe.

A 2 $\mu$l sample of the thus prepared Tp lysate is spread over the central 5 mm circular portion of a 10 mm cellulose acetate filter stock disc. The lysate is allowed to air dry at room temperature for one hour. A control disc is prepared by treatment with carbonate buffer only.

For serologic test for treponemal antibody in human serum:

Step 1. Unheated serum specimen is mixed in a $11 \times 75$ mm tube with sorbent—0.02 ml serum plus 0.08 ml sorbent—and left standing at room temperature 5 minutes. Tris HCl buffer pH 8.4 with 0.25% Tween 20 is added to a final volume of 0.8 ml. The final serum dilution for test is 1/40.

Step 2. The adsorbent-Tp plus the control adsorbent are added to the serum dilution tube and the tube is shaken 30 minutes on a horizontal platform shaker.

Step 3. The adsorbent-Tp and control are transferred to a wash tube containing 0.8 ml Tris-HCl buffer and shaken for 5 minutes.

Step 4. The adsorbent-Tp and control are transferred to a tube containing goat antibody to human immunoglobulins labeled with fluorescein isothiocyanate optimally diluted in 0.8 ml Tris-HCl buffer. The tube is shaken 30 minutes.

Step 5. The adsorbent-Tp and control are transferred to a wash tube and shaken as in Step 2.

Step 6. The specific fluorescence of the adsorbent-Tp is measured in a fluorometer (International Diagnostic Technology, Santa Clara, California). The $\Delta$OD, fluorescence of adsorbed-Tp minus control adsorbent, is checked against a standard curve of $\Delta$OD vs known positive FTA titers. A cut off value for positive results is established on the standard curve by test of FTA-ABS (National Center for Disease Control—1+reading standard) calibrator serum. The amount of antibody (titer) in the specimen is determined by extrapolation from the curve.

A standard curve with the FTA-ABS national standard cut off value is shown in the FIGURE. In practice, a three-point standard curve may be used; one point maximum reactive-positive serum, one point normal-negative serum, and one point the cut off value (reading standard) between negative and positive.

EXAMPLE 2

The procedure of this example is similar to the procedure of Example 1 except that the discs are replaced with solid glass spheres from 3–5 mm in diameter. The beads are coated with Tp lysate by immersion followed by thorough draining and air drying at room temperature. Controls are treated with carbonate buffer only.

Similar results are obtained when the glass spheres are replaced with polycarbonate or polystyrene spheres.

EXAMPLE 3

The procedure of Example 1 is repeated except that the fluorescent labeled antigen-antibody conjugate is eluted from the discs after Step 5 by placing the adsorbents in a tube containing 5.0 M potassium iodide or 3.0 M potassium isothiocyanate in Tris/HCl buffer pH 8.4 for 10 minutes under shaking.

The fluorescence of the eluting fluid is measured in an Ames Fluoro-Colorimeter, Miles Laboratories, Elkhart, Indiana or a Turner Fluorometer, G. K. Turner Associates, Palo Alto, California.

EXAMPLE 4

Solid spheres are an alternative to flat disc adsorbents transported through the tubes. The test procedure is the same as that given in Example 1 and 3 except that two sets of all tubes to permit handling spheres are used (1) a test set and (2) a control set. The wash volumes (Steps 3 and 5) are increased to 1.6 ml to accommodate the larger surface sera of the adsorbents. The adsorbent-Tp sphere is transported through the test and the control is transported through the control set. The difference in fluorescence (Example 1 and 3) counts per minute (see below) or optical density (see below) between test and control adsorbents is a measure of specimen positivity.

The presence of a conjugate formed between positive human serum and the adsorbent-Tp may be detected and measured by a radiolabeled antibody to human immunoglobulins. The protocol is essentially that given in Example 1. The adsorbent-Tp is placed in (transported through) serum dilution and wash tubes. The step 4 tube in this example, however, contains an optimal dilution of animal antibody human immunoglobulins labeled with iodine-125. Alternatively, other radiolabels such as sulfur 35 and beta emitters tritium 3 or carbon 14 may be used. As in Example 1, the exact concentration (dilution) of the labeled antiimmunoglobulin cannot be stated for all cases and must be determined (standardized) for the commercial product used. The final step (Step 6 in Example 1) is to place the washed adsorbent-Tp with conjugate and radiolabel into a suitable well-type gamma counter (or into scintillation vials for beta count when the radiolabel is tritium 3 or carbon 14) and determine the $\Delta$ counts per minute ($\Delta$ cpm), counts per minute of adsorbent-Tp minus control adsorbent. The values may be checked against a standard curve of $\Delta$ cpm vs FTA equivalent titer as in Example 1. Alternatively, 3 points (standards) may be run to determine the cut-off for positive/negative specimens.

The presence of a conjugate may also be detected and measured by an enzyme labeled antibody to human immunoglobulins. The first steps (Steps 1, 2 and 3) are the same as those in Example 1. The Step 4 tube in this system, however, contains an optimal dilution of animal antibody to human immunoglobulins labeled with alkaline phosphatase. The washed adsorbent-Tp and control adsorbent are separated and placed into two tubes for Step 6—a test (adsorbent-Tp) tube and a control (control adsorbent) tube. Each contains 0.8 ml of an optimum dilution of para-nitrophenyl phosphate in tris/HCl pH 8.4. The tubes are shaken 30 minutes at room temperature. The adsorbent-Tp and adsorbent-control removed from the respective tube and 0.2 ml 2 N NaOH is added to each tube. The tubes are shaken an additional 5 minutes. The $\Delta$OD determined spectrophotometrically at 405 nm, test tube OD minus control tube OD is checked against a standard curve of $\Delta$OD vs FTA titers as in Example 1. Alternatively 3 points (standards) may be run to determine the cut-off for positive/negative specimens.

What is claimed is:

1. A serological method for determining the presence of *Treponema pallidum* antibodies in human serum which comprises diluting the serum to be tested in physiological saline solution to a dilution of from 1:20 to 1:100, and thereafter incubating the diluted serum with a lysate of *Treponema pallidum* adsorbed on an inert adsorbent to form an antigen-antibody conjugate when said antibodies are present, and detecting the presence of said conjugate.

2. A serological method as claimed in claim 1, wherein the presence of the conjugate is detected by reaction with an antibody to human immunoglobulins, said antibody labeled with a chemical which fluoresces when exposed to ultraviolet light.

3. A method as in claim 2, wherein the chemical label is selected from the group consisting of fluorescein, rhodamine and auramine.

4. A serological method as claimed in claim 1, wherein the presence of the conjugate is detected by reaction with an antibody to human immunoglobulins, said antibody labeled with an enzyme.

5. A method as in claim 4, wherein the enzyme is selected from the group consisting of peroxidase, B-glucuronidase, B-D-glucosidase, B-D-galactosidase, urease, glucose oxidase plus peroxidase, galactose oxidase plus peroxidase, alkaline phosphatase, and acid phosphatase.

6. A serological method as in claim 1, wherein the presence of the conjugate is detected by reaction with an antibody to human immunoglobulins labeled with a radioactive element.

7. A method as in claim 6, wherein the radioactive element label is selected from the group consisting of $^{14}C$, $^{125}I$, $^{131}I$, and $^{35}S$.

8. A method as in any of claims 2–7 wherein the animal antibody is directed specifically to human immunoglobulin G or to human immunoglobulin M.

* * * * *